US005840251A

United States Patent [19]
Iwaki

[11] Patent Number: 5,840,251
[45] Date of Patent: Nov. 24, 1998

[54] DEVICE AND METHOD FOR CLEANING, DISINFECTING AND DRYING AN ENDOSCOPE

[75] Inventor: Yasuo Iwaki, Moriyama, Japan

[73] Assignee: Nitto Medical Corporation, Osaka, Japan

[21] Appl. No.: 742,061

[22] Filed: Oct. 31, 1996

[30] Foreign Application Priority Data

Oct. 31, 1995 [JP] Japan ..................................... 7-308378
Aug. 8, 1996 [JP] Japan ..................................... 8-227659

[51] Int. Cl.⁶ .............................. A01N 1/00; G05B 1/00; A61L 2/00; E04H 15/26
[52] U.S. Cl. ............................ 422/36; 422/105; 422/116; 422/294; 422/297; 422/300; 134/99.1; 134/104.2; 134/169 R; 134/170
[58] Field of Search .............................. 422/36, 297, 116, 422/294, 105, 300; 134/99, 104.2, 169, 170

[56] References Cited

U.S. PATENT DOCUMENTS

| | | | |
|---|---|---|---|
| 4,667,691 | 5/1987 | Sasa ........................................ | 134/169 |
| 5,091,343 | 2/1992 | Schneider et al. ....................... | 422/297 |
| 5,133,374 | 7/1992 | Druding et al. ...................... | 134/104.2 |
| 5,234,832 | 8/1993 | Disch et al. ............................. | 435/264 |

*Primary Examiner*—W. Gary Jones
*Assistant Examiner*—Jeffrey Fredman
*Attorney, Agent, or Firm*—Whitham, Curtis & Whitham

[57] ABSTRACT

A portion of the endoscope that has been withdrawn from the human body is inserted into the tubular body of the device and pressurized water, a liquid detergent, a liquid disinfectant and air are sequentially forced through a water injecting pipe, an inlet pipe and injection pipes that communicate with the tubular body, whereby not only the outer surface of the endoscope but also the inner ducts through it are cleaned, disinfected and dried in a convenient and safe manner.

19 Claims, 3 Drawing Sheets

DEVICE AND METHOD FOR CLEANING, DISINFECTING AND DRYING AN ENDOSCOPE

BACKGROUND OF THE INVENTION

1. Field of the Invention

The present invention relates to a device for cleaning, disinfecting and drying an endoscope that is used for examining the interior of a living body in medical diagnostic and treatment procedures. The invention also relates to a method of cleaning, disinfecting and drying the endoscope using the device.

2. Description of the Related Art

The recent advances in the technology of the endoscope for use in medical practices have been remarkable and the extent of their applicability ranging from testing through diagnosis to treatment has contributed a lot to the advances in medicine.

The endoscope is used in various organs of the human body which cover a wide scope including the digestive, respiratory, urinary and otorhinolaryngological systems, as well as gynecological and orthopedics systems.

The endoscope is used in these wide areas of medicine are so costly that they are not simply discarded after use but applied successively to many patients. Hence, an endoscope used with one patient must be thoroughly cleaned and disinfected before it is applied to another patient.

Since the endoscope is expensive, medical institutions such as small hospitals cannot afford to buy many endoscopes and the limited number of endoscopes are used for many patients. With limited availability of personnel in small hospitals, it has been extremely difficult to accomplish thorough cleaning and disinfection of the endoscope.

In big hospitals, automatic cleaning-disinfecting machines costing several thousand dollar are employed but, in fact, the current procedure of disinfecting the endoscope which has been used to examine one patient merely consists of washing off the deposit and dipping the endoscope in a liquid disinfectant. However, the disinfected endoscope is not completely dried before it is used for another patient.

This presents a potential hazard of causing secondary infection of bacteria, viruses and other pathogens from one patient to another. In addition, there is a possibility of cross-infection from patients to medical staff including doctors and nurses. As a further problem, the disinfectant (typically glutaraldehyde) evolves a noxious gas. Thus, there is a great concern on the safety of disinfecting operations.

SUMMARY OF THE INVENTION

The present invention has been accomplished under these circumstances and has as an object providing a device for cleaning, disinfecting and drying the endoscope which is cheap enough to be purchased by medium- and small-size hospitals and clinics, which can be connected to the endoscope in a short time and at low cost, and which permits the subsequent cleaning, disinfecting and drying operations to be performed safely without touching the contaminated endoscope.

According to a first aspect of the invention, there is provided a device for cleaning, disinfecting and drying an endoscope comprising: a tubular body having a receptacle on a top thereof for receiving a portion of an endoscope that has been withdrawn from a human body, and an outlet on a bottom thereof; an inlet pipe that extends from an upper part of the tubular body to be connected to a faucet; a branch pipe branching from the inlet pipe to be connected to a forceps socket of the endoscope; an injection pipe through which air, a detergent and a disinfectant are to be injected, the injection pipe being provided in the inlet and branch pipes; and a fluid reservoir provided within the tubular body at a site where a distal end of the portion of the endoscope which has been withdrawn from the human body is located.

According to a second aspect of the invention, there is provided a method of cleaning, disinfecting and drying an endoscope comprising the steps of: inserting a portion of an endoscope that has been withdrawn from a human body into a top receptacle of a tubular body; supplying pressurized water both into the tubular body and into a forceps duct running through the endoscope to wash the tubular body and forceps duct; collecting the water around a suction port at a distal end of the inserted portion of the endoscope; applying suction onto the collected water via the suction port to wash a suction duct running through the endoscope; injecting a detergent for cleaning an outer surface of the inserted portion and the forceps duct; collecting the detergent around the suction port; applying suction onto the collected detergent thereby cleaning the suction duct; injecting a disinfectant for disinfecting the outer surface of the inserted portion and the forceps duct of the endoscope; applying suction onto the collected disinfectant thereby disinfecting the suction duct; and forcing air so as to dry the outer surface of the inserted portion and the ducts of the endoscope.

DETAILED DESCRIPTION OF PREFERRED EMBODIMENTS

Embodiments of the present invention will now be described with reference to the accompanying drawings.

Figure 1:
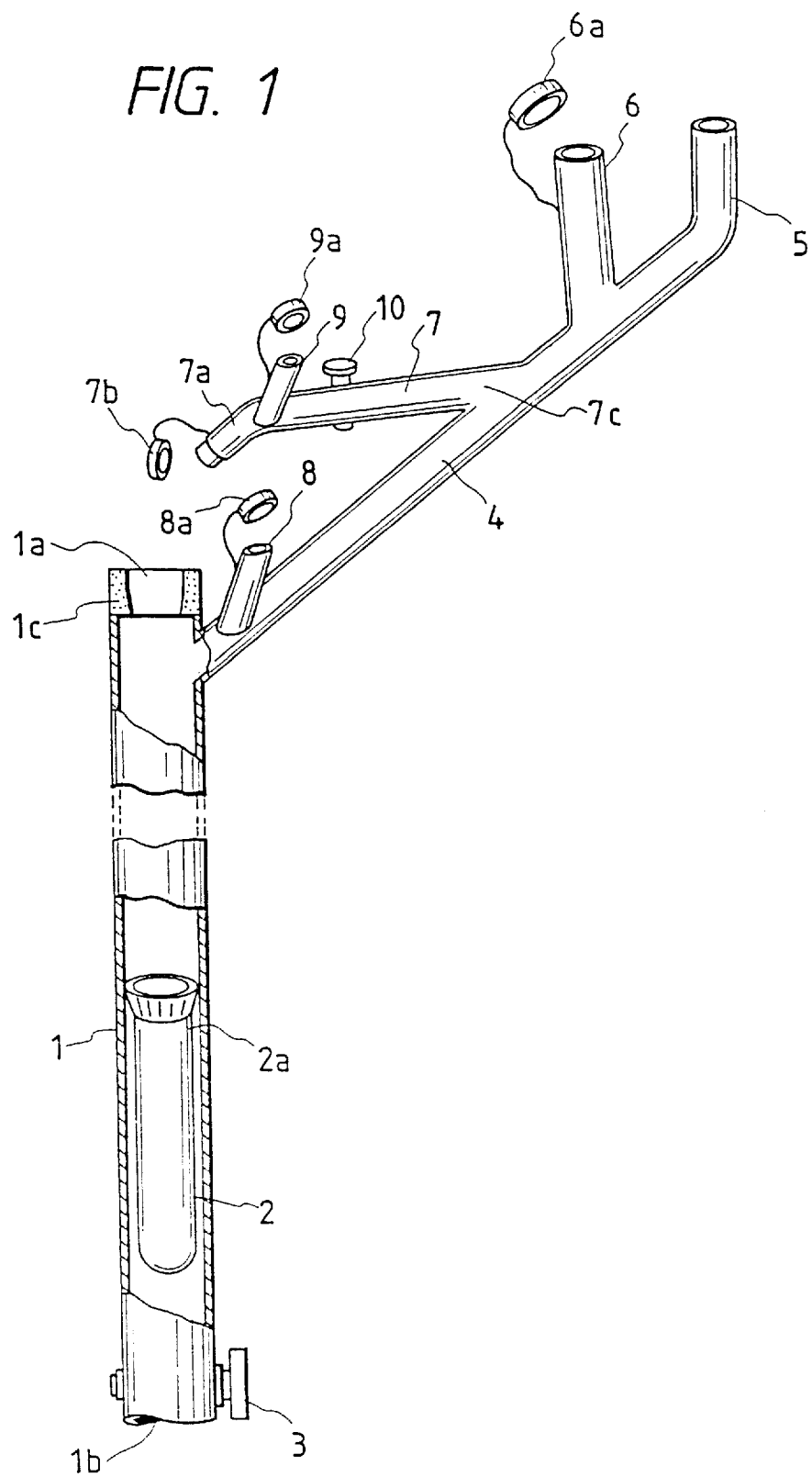
FIG. 1 is a partial fragmentary view of the device of the invention for cleaning, disinfecting and drying endoscopes.

FIG. 1 is a partial fragmentary view of the device of the invention for cleaning, disinfecting and drying an endoscope. The device comprises a tubular body 1 having such an inside diameter that it can receive a portion of an endoscope which has been withdrawn from the human body (as indicated by F in FIG. 2 which is to be described later) and that a cleaning solution, a liquid disinfectant and the like can be flowed as the portion F remains inserted into the tubular body 1. The tubular body 1 has a receptacle 1a on the top and an outlet 1b on the bottom through which running water, the cleaning solution, liquid disinfectant and the like are discharged.

Figure 2:
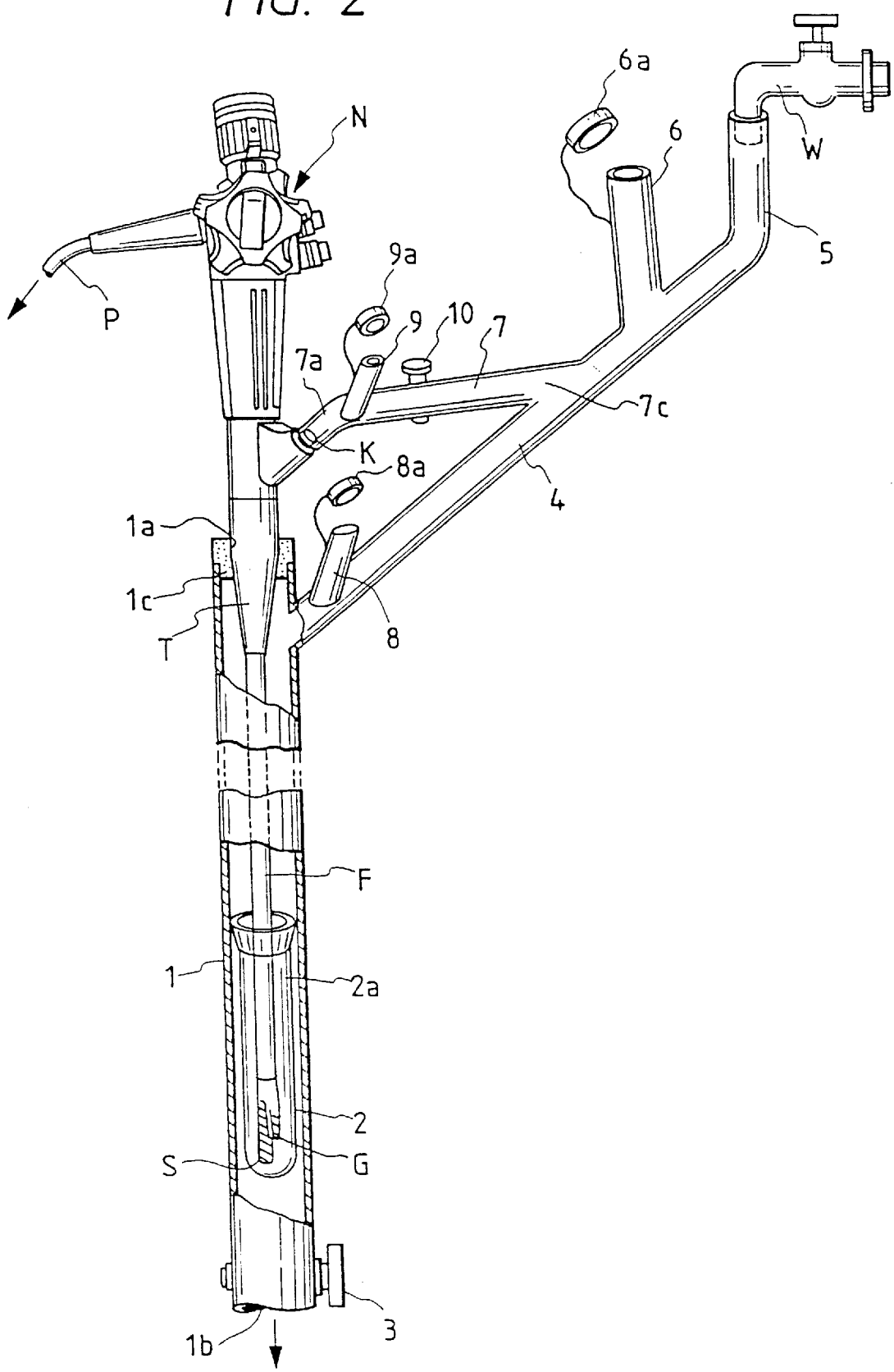
FIG. 2 is a partial fragmentary view illustrating the procedure of cleaning, disinfecting and drying an endoscope with the device of the invention.
Figure 3A:
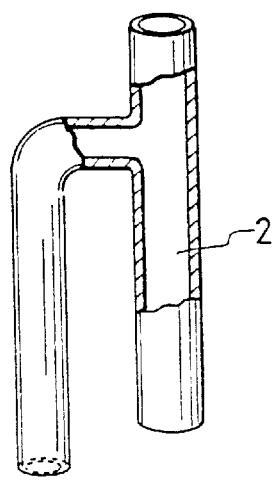
FIGS. 3(a) and 3(b) are partial fragmentary views showing modifications of the fluid reservoir in the invention device.
Figure 3B:
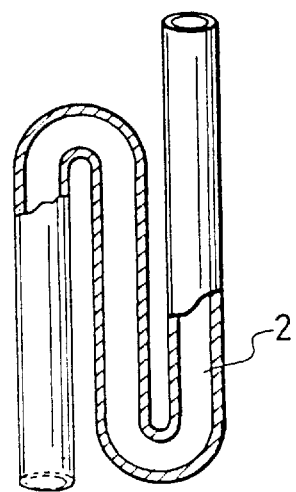

The receptacle 1a is fitted with a rubber seal ring 1c which ensures that the inserted portion F of the endoscope is fixed tightly with good seal; alternatively, the receptacle 1a has a bore with an inclined inner surface that fits the tapered portion T of the endoscope (see FIG. 2) with good seal. The tubular body 1 also has a fluid reservoir 2 at the site where the distal end S of the portion F of the inserted endoscope will be located. The top of the fluid reservoir 2 is shaped like a funnel that has a flared mouth with a plurality of effluent holes 2a that permit the passage of a fluid coming through the tubular body 1. Modified structures of the fluid reservoir 2 are shown in FIGS. 3(a) and 3(b). A valve 3 for regulating the effluent flow or stopping it is provided downstream of the fluid reservoir 2 in a position near the outlet 1b. Alternatively, a rubber stopper (not shown) may be provided to close the outlet 1b.

The upper part of the tubular body 1 has an inlet pipe 4 that communicates with the interior of the tubular body. The upper part of the inlet pipe 4 is provided not only with a water injecting pipe 5 which is to be connected to a faucet or the like for receiving cleaning water but also with an injection pipe 6. The lower part of the inlet pipe 4 is provided with an injection pipe 8; the inlet pipe 4 also has a branch pipe 7 that is provided with an injection pipe 9. The injection pipes 6, 8 and 9 are fitted with detachable caps 6a, 8a and 9a, respectively, for closing their openings.

In order to ensure that the insertion of the portion F of the endoscope and the flow of the cleaning water, liquid disinfectant and the like can be seen from the outside, the tubular body 1, inlet pipe 4, branch pipe 7 and (d the fluid reservoir 2 are preferably made of synthetic resin materials such as polyethylene, polyvinyl resin, polypropylene, polycarbonate, polyester, polystyrene, silicone, polyvinylidene chloride, polyvinyl acetate or the like that are transparent and which are flexible enough to easily bend or deflect.

The tubular body 1 into which the portion F of the endoscope is to be inserted should have an inside diameter of either 10 to 17 mm (If the diameter of the portion F is 3 to 10 mm) or 17 to 23 mm (if the diameter of the portion F is greater than 10 mm). This is in order to ensure that the water, detergent and disinfectant that have been introduced will flow uniformly to wet the entire part of the outer surface of portion F. The tubular body 1 has preferably a thickness of no more than 1 mm in order to ensure that running water will create a sufficient negative pressure within the body to cause its shrinkage or other deformations that allow for effective removal of the deposit on the outer surface of the endoscope. The branch pipe 7 terminates with a connector 7a for the forceps socket K. If the forceps socket K is not connected, the connector 7a is preferably closed with a cap 7b.

Being thusly constructed, the device of the invention may be used to clean, disinfect and dry an endoscope in the following manner (see FIG. 2).

The portion F of the endoscope N that has been withdrawn from a patient's body is inserted into the tubular body 1 through the receptacle 1a until the outer circumference of the tapered middle portion T has a good fit with the seal ring 1c to be secured tightly, while at the same time, the distal end S of the portion F is located within the fluid reservoir 2 of the tubular body 1.

In addition, the connector 7a of the branch pipe 7 is inserted into the forceps socket K and, thereafter, the openings of the injection pipes 6, 8 and 9 are closed with respective caps 6a, 8a and 9a.

In the next step, running water supplied at high pressure through the water injecting pipe 5 connected to a faucet W is allowed to flow into the inlet pipe 4 and the branch pipe 7, thence into the tubular body 1 and the forceps duct (not shown) in the endoscope for a continuous period of, say, ten odd seconds, whereby at least the "visible" contaminating deposit is washed away. Since a stop valve 10 or a tube typically made of silicone rubber which can be closed by manipulation with fingers or forceps is provided between a branched portion 7c of the branch pipe 7 and the injection pipe 9, the water collecting in the fluid reservoir 2 can be removed by applying suction through a port G that is open at the distal end S of the portion F and which communicates with the suction duct (not shown) in the endoscope.

Since the tubular body 1 contains the fluid reservoir 2 in the form of a test tube, with the effluent holes 2a perforated in the top of the fluid reservoir 2, the water supplied through the inlet pipe 4 to come down the tubular body 1 flows through the holes 2a to be discharged via the valve 3 if it is open. It should be noted that the fluid reservoir 2 holds constant amounts of water, detergent and disinfectant.

Following the washing step described above, chemical cleaning is performed to remove "invisible" organic contaminants such as protein and fat deposits. To this end, caps 8a and 9a are removed and a liquid detergent is injected or pressure sprayed into the injection pipes 8 and 9 such that it cleans the outer surface of the portion F of the inserted endoscope; after the injected liquid detergent fills the fluid reservoir 2, the stop valve 10 is closed or the silicone rubber tube (if used at all) is closed with fingers or forceps and suction is applied to have the liquid detergent flow through the forceps and suction ducts (neither shown) in the endoscope for cleaning them. The detergent used here is preferably a powerful medical enzyme detergent that accomplishes the desired cleaning within a few seconds.

To have the detergent washed off the outer surface of the portion F of the endoscope, as well as from its forceps and suction ducts, tap water is forced under pressure through the injection pipe 5 for a few seconds, thereby accomplishing physical rinse with the pressurized running water.

In the next step, a chemical disinfectant (ethanol) or strong acid water is similarly injected or pressure sprayed into the injection pipes 8 and 9 such that it disinfects the outer surface of the portion F of the inserted endoscope; after the injected liquid disinfectant fills the fluid reservoir 2, the stop valve 10 is closed or the silicone rubber tube (if used at all) is closed with fingers or forceps and suction is applied to disinfect the suction and forceps ducts. If the endoscope is also contaminated in the water feed duct (not shown), this must be cleaned and disinfected with a detergent and a disinfectant that are injected through a water supply port or bottle (neither shown).

If it is necessary to dry up the outer surface of the portion F of the inserted endoscope N, as well as the interior of the ducts through the endoscope, the caps 8a and 9a are fitted on the injection pipes 8 and 9 whereas the cap 6a is removed form the injection pipe 6, through which air is forced under pressure to accomplish rapid drying. The injection pipe 6 is provided to have air supplied under pressure with the water injecting pipe 5 remaining connected to the faucet W and this pipe 6 and the associated cap 6a may be eliminated if drying air is forced through the water injecting pipe 5.

If the patient with which the endoscope N has been used is a carrier of a virus such as hepatitis B or C virus or HIV virus, immersion disinfection must be performed using an enhanced-action disinfectant (glutaraldehyde) after cleaning has been effected in the manner described above using pressurized running water and a disinfectant. To this end, valve 3 is closed or a rubber stopper (not shown) is fitted on the outlet 1b and an enhanced-action disinfectant is injected through the injection pipe 6 or the water injecting pipe 5 (if the injection pipe 6 is not provided) such that the interior of the tubular body 1 and the forceps and suction ducts in the endoscope N are filled with the enhanced-action disinfectant for a specified time; thereafter, the valve 3 is opened or the rubber stopper is removed to have the disinfectant flow out, optionally followed by drying with pressure air in the manner already described above.

Since glutaraldehyde generates a toxic gas, its use involves a certain danger; however, according to the method just described above, the endoscope can be disinfected in a closed circuit without the risk of gas exposure. In addition to this safety feature, the immersion disinfection which is performed within the tubular system has the advantage that glutaraldehyde need be used in an amount which is less than a twentieth of the usual quantity, whereby the cost of disinfecting operations is significantly reduced.

As described on the foregoing pages, the present invention provides an inexpensive device with which an endoscope, as it has the connector portion coupled to a light source unit, can be cleaned, disinfected and dried in a convenient and safe manner once the endoscope is inserted into the tubular body of the device (i.e., without the need to detach or reinsert the endoscope for performing the individual operations). Thus, the invention offers great benefits not only to medical staff concerned with the operation of endoscopes but also to the many patients examined with endoscopes.

What is claimed is:

1. A device for cleaning, disinfecting and drying an endoscope, said endoscope having an insertion portion for being inserted into a patient and a forceps socket, said device comprising:
    a tubular body having a top, a bottom opposite said top, an upper part adjacent said top, a lower part adjacent said bottom, an outlet at said bottom and an opening at said top, said opening receiving said insertion portion of said endoscope;
    a water inlet pipe extending from said upper part of said tubular body;
    a branch pipe branching from said inlet pipe and connecting to said forceps socket of said endoscope;
    at least one injection pipe extending from at least one of said inlet pipe and said branch pipe, said at least one injecting pipe injecting at least one of air, a detergent and a disinfectant; and
    a fluid reservoir positioned within said tubular body at said lower part, said fluid reservoir receiving said insertion portion of said endoscope.

2. The device for cleaning, disinfecting and drying an endoscope according to claim 1, further comprising a rubber seal ring connected to said opening of said tubular body.

3. The device for cleaning, disinfecting and drying an endoscope according to claim 1, wherein said endoscope includes a tapered portion, and;
    said opening further including an inclined inner surface for contacting said tapered portion of said endoscope.

4. The device for cleaning, disinfecting and drying an endoscope according to claim 1, wherein said fluid reservoir includes a top having a funnel shape, said top including a flared mouth having a plurality of effluent holes.

5. The device for cleaning, disinfecting and drying an endoscope according to claim 1, further comprising a valve positioned between said fluid reservoir and said outlet, said valve regulating and stopping an effluent flow.

6. The device for cleaning, disinfecting and drying an endoscope according to claim 1, further comprising a rubber stopper for closing said outlet.

7. The device for cleaning, disinfecting and drying an endoscope according to claim 1, wherein said tubular body, inlet pipe, branch pipe and fluid reservoir comprise a transparent, flexible synthetic resin, said tubular body allowing an exterior and an interior of said endoscope to be cleaned simultaneously.

8. The device for cleaning, disinfecting and drying an endoscope according to claim 7, wherein said tubular body, inlet pipe, branch pipe and fluid reservoir comprise one of polyethylene, polyvinyl resin, polypropylene, polycarbonate, polyester, polystyrene, silicone, polyvinylidene chloride and polyvinyl acetate.

9. The device for cleaning, disinfecting and drying an endoscope according to claim 1, wherein said tubular body has an inner diameter of 10 to 17 mm and said insertion portion of said endoscope has an outer diameter of 3 to 10 mm.

10. The device for cleaning, disinfecting and drying an endoscope according to claim 1, wherein said tubular body has an inner diameter of 17 to 23 mm and said insertion portion of said endoscope has an outer diameter greater than 10 mm.

11. The device for cleaning, disinfecting and drying an endoscope according to claim 1, wherein said tubular body comprises a material having a thickness of no more than 1 mm.

12. The device for cleaning, disinfecting and drying an endoscope according to claim 1, wherein said inlet pipe includes a first end adjacent said tubular body and a second end opposite said first end, said device having a plurality of said injection pipes including:
    a first injection pipe, extending from said second end of said inlet pipe, through which air is supplied under pressure;
    a second injection pipe, extending from about said first end of said inlet pipe through which said detergent and said disinfectant are supplied; and
    a third injection pipe, extending from said branch pipe through which said detergent and said disinfectant are supplied.

13. The device for cleaning, disinfecting and drying an endoscope according to claim 12, further comprising a stop valve positioned on said branch pipe between said inlet pipe and said third injection pipe.

14. The device for cleaning, disinfecting and drying an endoscope according to claim 12, further comprising a tube comprising silicone rubber connected to said branch pipe.

15. A method of cleaning, disinfecting and drying an endoscope comprising:
    inserting a portion of an endoscope that has been withdrawn from a human body into a top receptacle of a tubular body;
    supplying pressurized water into a first path connected to the tubular body and into a second path connected to a forceps duct running through the endoscope, said water washing the tubular body and the forceps duct;
    providing means for collecting the water around a suction port at a distal end of the inserted portion of the endoscope;
    applying suction onto the water via the suction port to wash a suction duct running through the endoscope;
    injecting a detergent into said tubular body, said detergent cleaning an outer surface of the inserted portion and the forceps duct of the endoscope;
    providing means for collecting the detergent in an area around the suction port;
    applying suction onto the detergent thereby cleaning the suction duct;
    injecting a disinfectant into said tubular body, said disinfectant disinfecting the outer surface of the inserted portion of the endoscope and the forceps duct of the endoscope;

applying suction onto the disinfectant thereby disinfecting the suction duct;

forcing air into at least one of the first path and a third path connected to the tubular body to dry the outer surface of the inserted portion of the endoscope; and forcing air into the second path to dry the ducts of the endoscope.

16. The method of cleaning, disinfecting and drying an endoscope according to claim 15, wherein the steps of injecting said detergent and injecting said disinfectant comprise pressure spraying said detergent and said disinfectant, said tubular body allowing an exterior and an interior of said endoscope to be cleaned simultaneously.

17. The method of cleaning, disinfecting and drying an endoscope according to claim 15, wherein the step of injecting said disinfectant comprises injecting one of ethanol and a strong acid.

18. The method of cleaning, disinfecting and drying an endoscope according to claim 15, further comprising steps of:

closing one end of the tubular body;

filling an interior of the tubular body, forceps and suction ducts with an anti-virus disinfectant.

19. The method of cleaning, disinfecting and drying an endoscope according to claim 18, wherein the step of filling comprises filling said tubular body, forceps and suction ducts with glutaraldehyde.

* * * * *